US008362447B2

(12) United States Patent
Lambert

(10) Patent No.: US 8,362,447 B2
(45) Date of Patent: Jan. 29, 2013

(54) DEGRADABLE TAGGANT AND METHOD OF MAKING AND USING THEREOF

(75) Inventor: Christopher R. Lambert, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 202 days.

(21) Appl. No.: 12/668,938

(22) PCT Filed: Jul. 14, 2008

(86) PCT No.: PCT/US2008/070013
§ 371 (c)(1),
(2), (4) Date: Aug. 2, 2010

(87) PCT Pub. No.: WO2009/012238
PCT Pub. Date: Jan. 22, 2009

(65) Prior Publication Data
US 2010/0288943 A1 Nov. 18, 2010

Related U.S. Application Data

(60) Provisional application No. 60/949,689, filed on Jul. 13, 2007.

(51) Int. Cl.
*G01N 21/64* (2006.01)
(52) U.S. Cl. .................................................. 250/459.1
(58) Field of Classification Search ............... 250/459.1
See application file for complete search history.

(56) References Cited

U.S. PATENT DOCUMENTS

| 4,197,104 | A | | 4/1980 | Krystyniak et al. |
| 5,972,638 | A | * | 10/1999 | Burlage et al. ............... 435/29 |
| 6,165,609 | A | | 12/2000 | Curatolo |
| 6,514,617 | B1 | | 2/2003 | Hubbard et al. |
| 6,818,919 | B2 | * | 11/2004 | Robeson et al. ............... 257/40 |
| 6,899,827 | B2 | | 5/2005 | Lauf et al. |
| 7,247,443 | B2 | * | 7/2007 | Su ..................................... 435/7.1 |
| 2001/0035261 | A1 | * | 11/2001 | Banahan ....................... 156/277 |
| 2003/0036201 | A1 | * | 2/2003 | Nelson et al. ................... 436/56 |
| 2004/0091635 | A1 | | 5/2004 | Yaniv |
| 2004/0233465 | A1 | * | 11/2004 | Coyle et al. .................... 358/1.9 |
| 2011/0135734 | A1 | * | 6/2011 | Magdassi et al. ............. 424/489 |

OTHER PUBLICATIONS

International Preliminary Report on Patentability and the Written Opinion of the International Searching Authority dated Jan. 19, 2010, from parent application US2008/070013 filed on Jul. 14, 2008, which has a priority date of Jul. 13, 2007.
International Search Report dated Mar. 20, 2009 from corresponding international application No. PCT/US2008/070013.

* cited by examiner

*Primary Examiner* — Kiho Kim
(74) *Attorney, Agent, or Firm* — Burns & Levinson LLP; Jacob N. Erlich; Janine M. Susan

(57) ABSTRACT

The present invention is a low-cost, easily deployed, degradable taggant that can be dispersed over a wide area to serve as a witness to activity in the area and for queuing of other sensors. The taggant enables nearly real-time change detection within the treated area using one or more simple optical sensing techniques.

20 Claims, 8 Drawing Sheets

DEGRADABLE TAGGANT AND METHOD OF MAKING AND USING THEREOF

CROSS-REFERENCE TO RELATED APPLICATIONS

This application is a U.S. national stage application under 35 U.S.C. 371 of co-pending International Application No. PCT/US08/070,013 filed Jul. 14, 2008, which in turn claims priority to U.S. Provisional Application No. 60/949,689 filed Jul. 13, 2007, both of which are incorporated by reference herein in their entirety for all purposes.

BACKGROUND

Traditional warfare, with accepted rules of engagement, appears to have given way to unconventional, asymmetrical warfare. One asymmetric threat that is proving difficult to counter and defeat is the improvised explosive devise (TED), commonly known as the "roadside bomb." Today, IEDs are the major cause of combat casualties. They are the most effective way to cause the most harm at the least cost and are also often augmented with conventional mines on routes and soft shoulders that are vulnerable to surface-laid and dug-in anti-vehicle and antipersonnel mines.

In the past, IEDs were typically laid at night, often in craters left by previously detonated IEDs, and used a myriad of triggering techniques: cell phones or pagers, garage door openers, pressure plates or strips, etc. Today, this is no longer the case. Hand triggered IEDs are laid at all hours of the day in order to provide the triggerman with ample illumination for target acquisition and ordnance detonation. To be effective, IED detection technologies and strategies must allow for day/night and low visibility operations.

SUMMARY

The present invention is a low-cost, easily deployed, degradable taggant that can be dispersed over a wide area to serve as a witness to activity in the area and for queuing of other sensors. The taggant enables nearly real-time change detection within the treated area using one or more simple optical sensing techniques.

DETAILED DESCRIPTION OF PREFERRED EMBODIMENTS

Figure 1C:
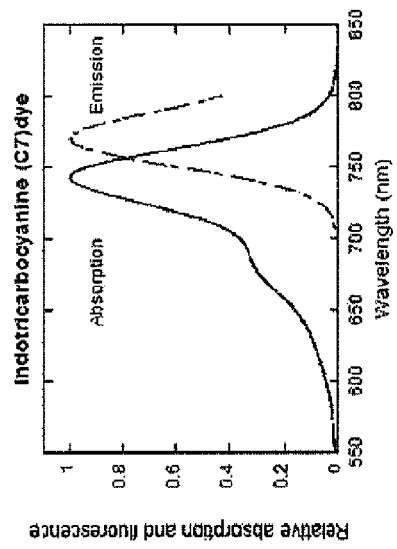
FIG. 1c is a graph of the absorption and fluorescence spectra of indotricarbocyanine (C7)
Figure 1B:
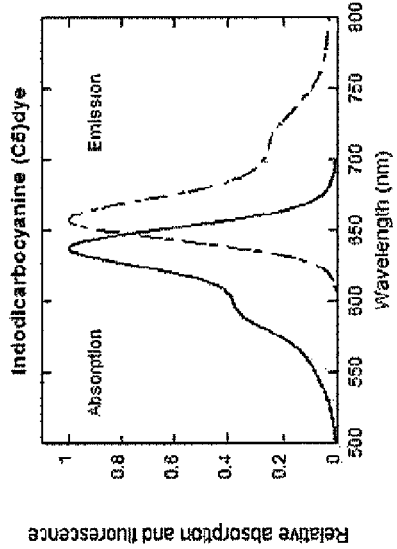
FIG. 1b is a graph of the absorption and fluorescence spectra of indodicarbocyanine (C5)
Figure 1A:
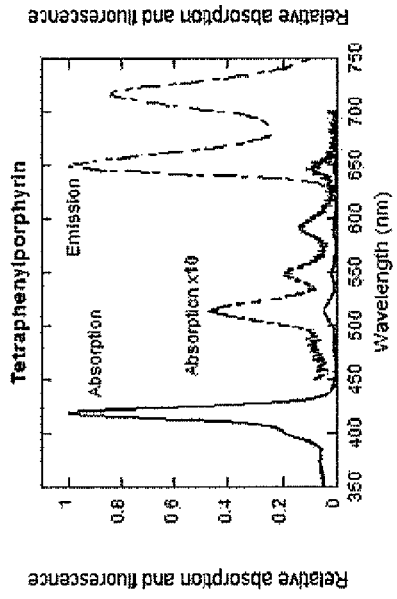
FIG. 1a is a graph of the absorption and fluorescence spectra of tetraphenylporphyrin (TPP)

Currently the most effective way to detect an IED is through visual observation of the local environment and the population. This is accomplished by looking for objects that appear new to the environment or out of place, areas where the ground looks to have been recently disturbed and local people who appear nervous or disperse when approached. This visual observation method is a technique known as change detection, that is, the identification of changes in the environment that either identify the TED directly, or identify tell-tale characteristics associated with IED emplacement (e.g. digging, new objects in the environment, new paths leading to an existing object, etc.). Change detection is a very powerful tool that can be used to counter asymmetric threats, but to be maximally effective it must be sensitive to subtle changes in a very noisy background while minimizing both false positives and false negatives.

For IED identification in highly cluttered places, the most effective change detection technique is one that employs fading memory, i.e., a witness taggant whose signal fades (degrades) with time. A particularly simple optical change detection scheme works by comparing cells within two images of a specific area, separated in time. The system may operate either by detecting a disturbance in the deployed region or the presence of a taggant in the non deployed region. Coincident detection of a disturbance and the presence of a taggant increases the probability that a disturbance has occurred. It is also possible to deploy taggant underground. If for example a road surface is repaired and the taggant is deployed beneath the surface then the presence of taggant would indicate a disturbance. Casual inspection of the surface does not show the presence of taggant. However wavelength and time resolved fluorescence imaging makes the change readily apparent.

In a similar fashion one can look for changes between two scenes where in a later scene something has been removed or altered. For example, with the taggant deployed on a road, the material fluoresces when excited with UV light. The material is dispersed uniformly across the road and the fluorescence image and the temporally resolved image are typical of a uniformly dispersed taggant. At a later time a hole is dug in the road which disturbs the fluorescent powder, and then the hole is refilled, While it is difficult to see the change in the surface by comparing images obtained before and after the disturbance is easily detected. To "reset" the area, additional powder would be sprayed over the road so that future "changes" can be detected. This can present a problem if the taggant does not degrade with time (e.g. have a fading memory). As more and more taggant is dispersed, the ground becomes contaminated to a degree that the signal to noise ratio of the "changes" is so low that it becomes virtually impossible to detect. The best solution is to have a taggant that can be turned off at some preset time, for example just prior to re-spraying the area. Here each new application would be laid down on a pristine surface with no previous tagging contaminants. While a passive, binary (on/off) taggant is likely impossible to manufacture, it is possible to design the tagging compound in such a way as to allow it to disappear over time, from hours to weeks.

Because the level of background "noise" exponentially increases in urban or populated areas, the degradation time of the taggant should be varied depending on the area of operation (AO). Since every AO has its characteristic IED tactics, a variable degradation time will allow the taggant to be optimally tailored to maximize its effectiveness.

Additional advantageous taggant characteristics would be:

Extremely low manufacturing costs since the taggant will be dispersed over large areas numerous times;

Easily deployed and provides uniform coverage using relatively simple equipment (like paint sprayers or crop dusters);

Signal when viewed by appropriate sensing system must have a good signal to noise ratio and good background contrast;

Taggant signal should be dim cult to reverse engineer or should provide a coded return (anti-spoof characteristic);

The taggant should be difficult to detect by the unaided eye.

I. Composition

The degradable taggant of the present invention is developed by combining two low-cost, highly stable compounds: laser dyes and titanium dioxide or silicon dioxide. Laser dyes are a desirable choice because they are readily available, come in a myriad of absorption/emission wavelengths, have well defined fluorescence times, and can be chosen to have a very low production cost. Titanium dioxide, or $TiO_2$ (commonly found in house paints, sun tan lotions, and tooth paste), is a white powder that is highly reflective, is a strong photocatalyst under ultraviolet (UV) light, and because of its wide commercial use, is produced in great quantities at very low cost. While both the laser dyes and $TiO_2$ are individually very stable, when $TiO_2$ is coated with a laser dye the compound becomes photoreactive, that its, it degrades over time when exposed to light through the process of photobleaching.

The laser dye coated $TiO_2$ taggant has a number of highly desirable characteristics for the proposed application:

Taggant is completely passive, both in generating a return signal and in the method of degradation.

It will be nearly undetectable by the unaided eye making it difficult to detect that an area has been treated.

Because it is a powder, it can be applied using conventional spraying equipment. Additionally, it can be suspended in a liquid such as water to minimize unwanted dispersion caused by the wind.

Taggants can be created with a variety of absorption/emission wavelengths. By mixing several taggant "colors" together a coded signal can be created that makes spoofing virtually impossible and provides other useful intelligence.

Fluorescence signal has two detection modes, absorption/emission band separation and fluorescent lifetime. Sensing both enhances SNR and adds an additional level of security.

An odorizer can be used to allow canine detection of the taggant.

Laser dyes and sensing techniques can be selected to eliminate sun blinding, allowing change detection sensing to occur both day and night.

The taggants can be made of a number of different components, substrates, derivatizations of the substrate, dye combinations, antioxidants and other stability or spectral modifiers. Even with only two dyes it is possible to modify all the other components to make forgery of the particle difficult.

The substrate may be a semiconductor (titanium dioxide) or an insulator (silica or a polymer such as PVA or hydroxycellulose). The substrate may be composed of gold nanoparticles (typically 300 nm in diameter). By controlling the spacing between the dye and the nanoparticles the fluorescence intensity may be increased.

The substrate may be derivatized to control its ability to "solubilize" the dye on the surface and to give it the ability to stick to clothing or skin.

The dye combination and the concentration of dyes controls the emission spectrum of the dyes and depending on the degradation of the taggant, changes with time. This change may be detected by monitoring the relative intensities of emission bands and ratioing the result or by monitoring the fluorescence lifetimes of the dyes on the surface or by a combination of these methods. Ratiometric imaging and temporal measurements reduces the effect light scattering and increases the security of the measurement and the selectivity of the measurement. It is possible to fabricate a complex taggant using only two dyes but the complexity is increased dramatically by using three or more dyes.

Attachment of the dyes to a substrate particle may be through physisorption, electrostatic interactions or through covalent attachment. Electrostatic interactions and covalent attachment increases the difficulty of duplicating the taggant by an unauthorized individual.

Addition of antioxidants changes the stability of the dyes and also modifies the spectroscopy through a mechanism of photoelectron transfer. Incorporation of saturatable absorbers modifies the emission of the dyes. The saturatable absorber does not itself fluoresce but changes the emission spectrum of the taggant.

In one embodiment, a pressure sensitive taggant may be fabricated using a crushable capsule. The capsule contains a solution of fluorophore and a quencher such as sodium iodide. The capsule does not fluoresce. Upon crushing the capsule the solution leaks out, the solvent evaporates and the fluorophore now fluoresces.

II. Method of Use

Once an area of interest has been tagged, activity in that area will result in a change in the taggant's areal distribution. For example, digging will cause the taggant to be mixed with the excavated dirt. When the dirt is replaced, the taggant's distribution in that area will be significantly different both spatially and temporally. Here, change detection, using ratiometric fluorescence spectroscopic techniques, can be accomplished by either comparing scanned data from two different times, or by performing a spatial correlation to look for adjacent areas with significantly different intensities. This same change detection technique can be used to detect objects added to an area of interest after it has been tagged. Since the new object will not be covered by the taggant, its return signal intensity will be zero. Again, time series comparisons or areal correlation techniques will quickly identify the new object (even if an attempt is made to artificially tag the object by pacing it in contact with objects in the area that are covered with taggant).

A very important characteristic of the taggant is that individuals walking around in a tagged area will not only alter the taggant's distribution (which will be detected), they will also pickup taggant on their shoes and clothing. Because the taggant fluoresces, and is coded, these individuals can be quickly identified and the specific AO where they performed activity located. Additionally, by adding an odorizer to the taggant, canines can be used to track and locate individuals who walked through a tagged area. Coded taggant found on the cloths of individuals that correlates to an AO where an IED was found or triggered would provide valuable physical evidence. The system of the present invention could be used by individuals on foot, operated from moving vehicles, and deployed on unmanned ground and air vehicles.

III. Properties

The degradable taggant of the present invention has the following properties: the taggant is a particulate which simplifies the deposition of the material. A combination of fluorophores is used which facilitates ratiometric measurement of the fluorescence and allows the particles to be coded. By characterizing as few as five fluorophores it is possible to combine three of these compounds in ten different ways, or two of these compounds in thirty different ways. Coding the taggant reduces the ability to forge the particles and also allows for additional intelligence data to be collected. The stability of the particles is dependent on the concentration of fluorophore applied to the particle surface and to the presence of simple antioxidant molecules formulated with the dyes. It is possible with this methodology to control the timescale over which the taggant degrades.

The fluorophores chosen emit fluorescence in the red to near infra red region of the electromagnetic spectrum. The eye is least sensitive to this region of the spectrum, however, it is a region that is readily imaged by commercial hyperspectral imaging devices.

Dye Selection

Figure 3:
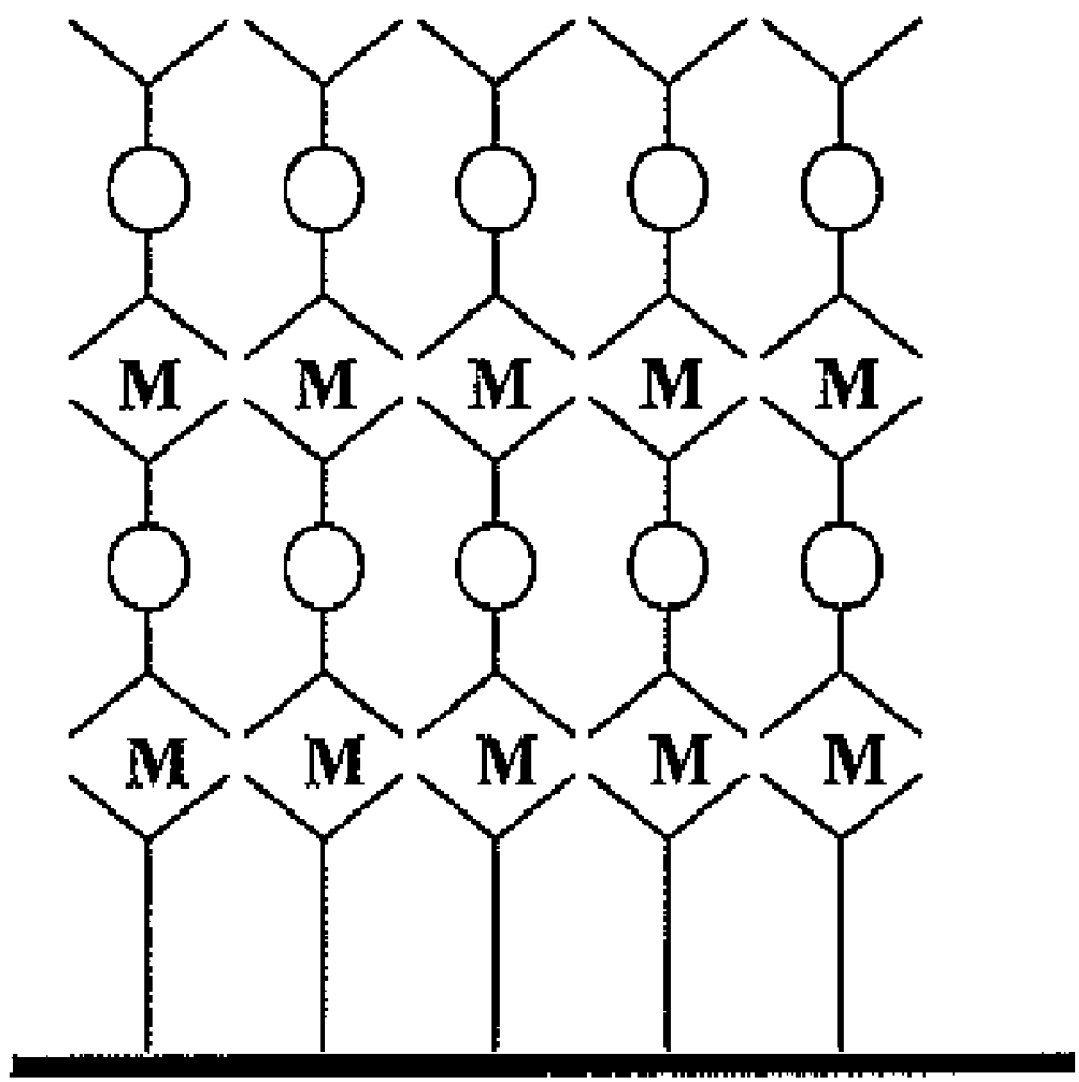
FIG. 3 shows a schematic of fluorophores assembled with non covalent linkage between molecules.
Figure 4:
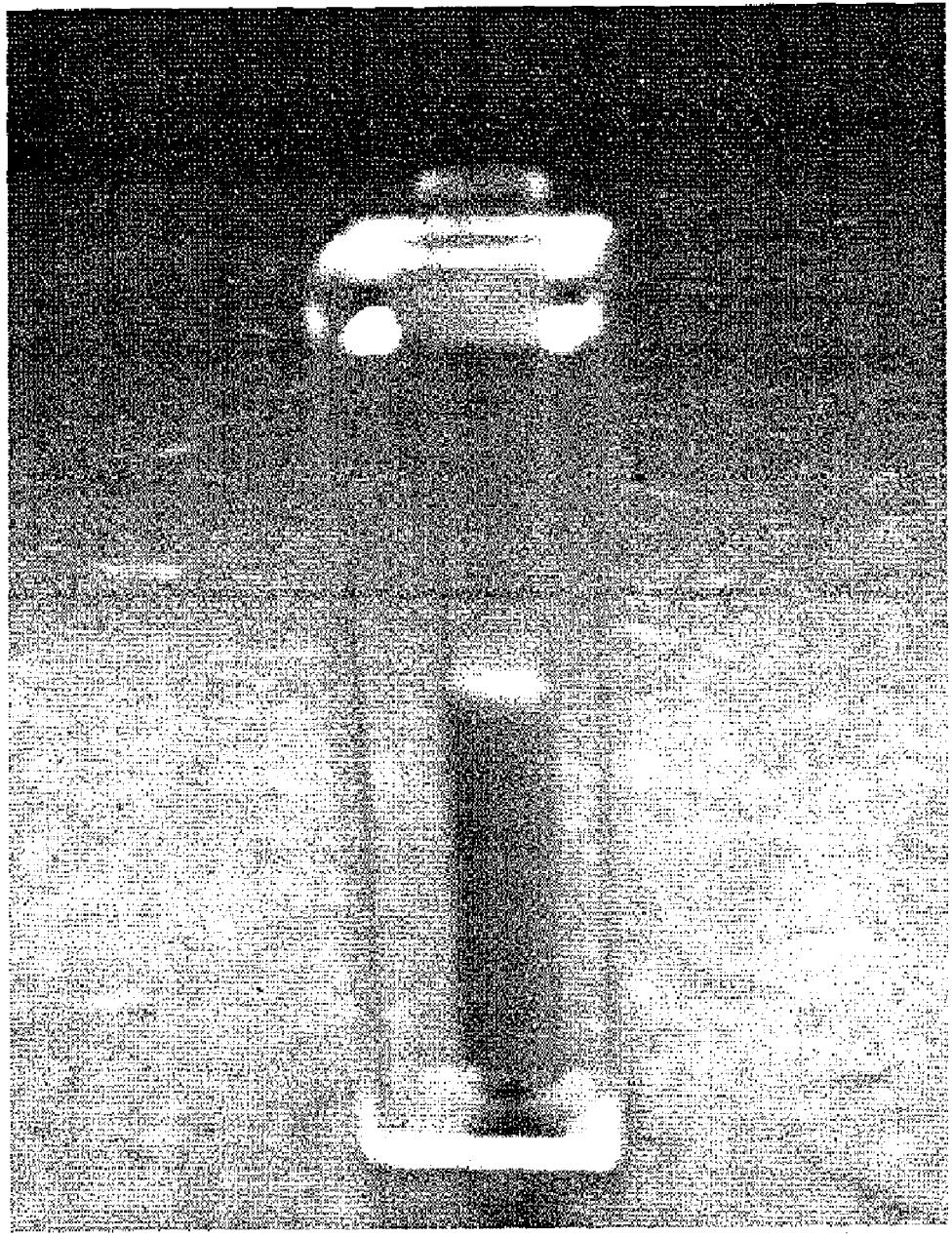
FIG. 4 is a photograph of a modified cuvette shown where the sample is contained in an inner tube within a conventional cuvette.
Figure 5A:
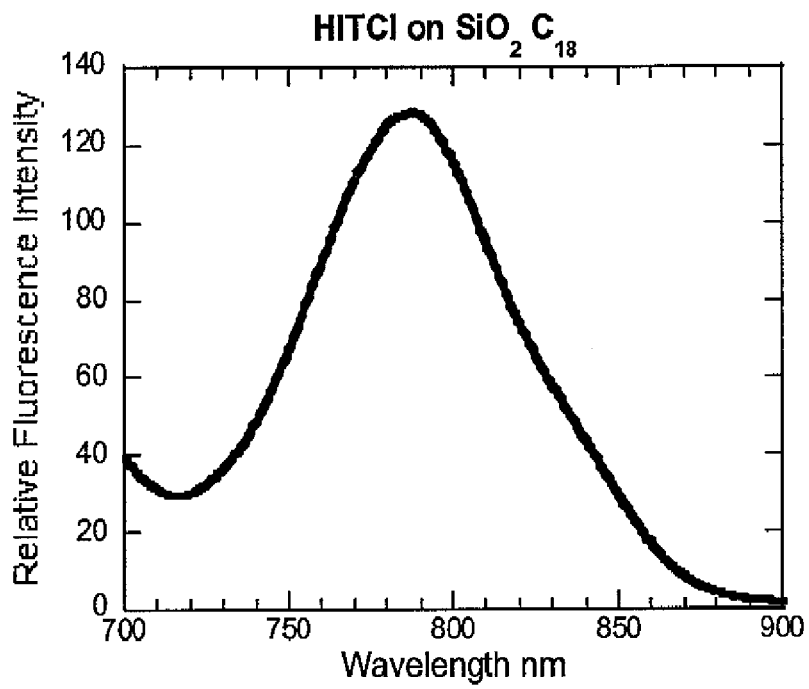
FIG. 5a is a graph of the fluorescence spectra of HITCI on $SiO_2C_{18}$.
Figure 5B:
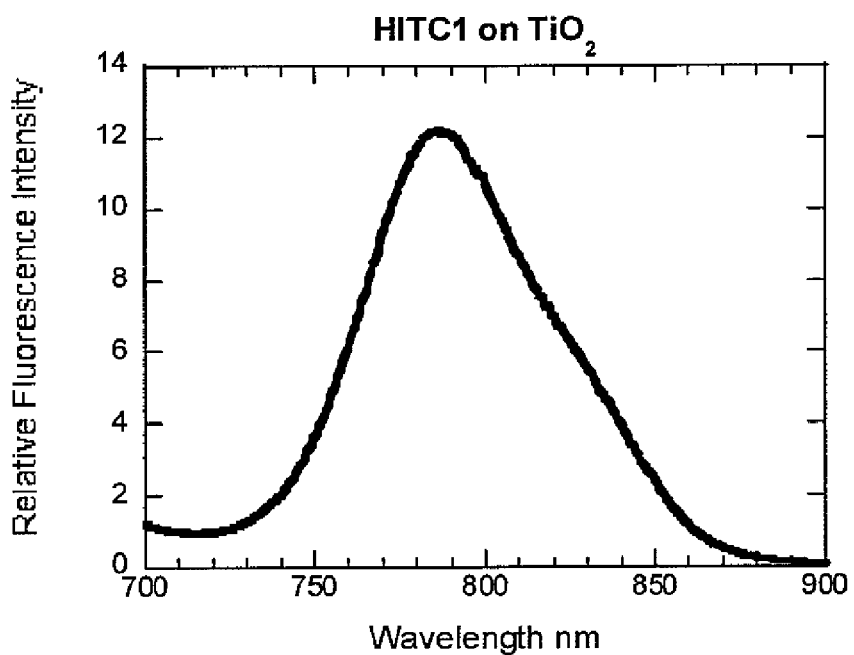
FIG. 5b is a graph of the fluorescence spectra of HITCI on $TiO_2$.

The dyes used in the present invention are selected from a group consisting of three commonly available red/NIR dyes and their photochemistry on titanium dioxide particles. These are tetraphenylporphyrin (TPP), indodicarbocyanine (C5) and indotricarbocyanine (C7). The absorption and fluorescence spectra of these molecules are shown in FIG. 3. Other dyes which may be used may be found in Brackmann, U. (2000) "Lambdachrome® Laser Dyes", Lambda Physik AG•D-37079 Goettingen•Germany (which is incorporated by reference herein in its entirety).

Emission and excitation spectra for a total of fourteen dyes have been obtained. These spectra have been acquired in solution, adsorbed onto $TiO_2$ particles and on Silica particles. Some spectra have also been acquired on the derivatized particles.

Figure 6:
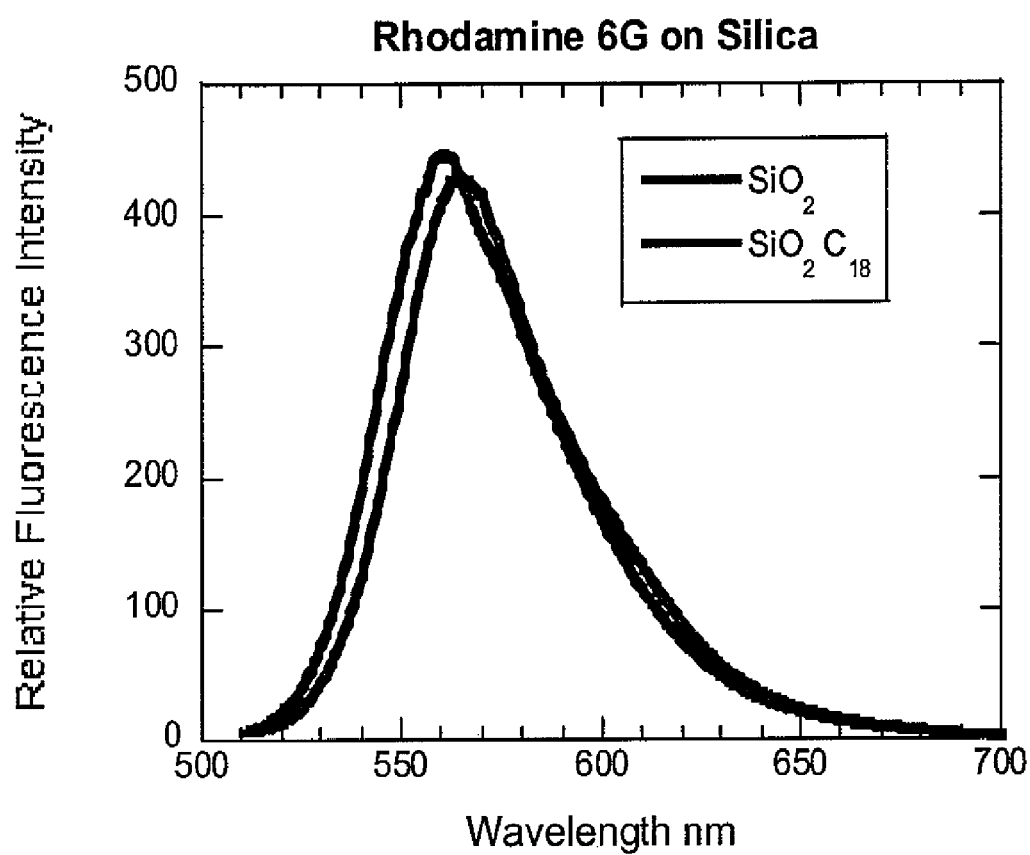
FIG. 6 is a graph of the fluorescence spectra of Rhodamine 6G on silica.

The structures and the emission spectra of these dyes are shown below:

Emission spectra for HITCI on $C_{18}$ derivatized silica and on $TiO_2$ ($\lambda_{exc}$ 665 nm) are shown in FIGS. 6a and b. HITCI on bare $SiO_2$ is blue shifted by about 20 nm compared to the $C_{18}$ derivatized substrate.

LD 700

| | |
|---|---|
| CAS: | 63561-42-2 |
| Molecular Weight: | 538.95 g/mol |
| Molar Absorption Coefficient: | $9.25 \times 10^4$ L mol$^{-1}$ cm$^{-1}$ @ 643 nm |

Emission in ethanol at 670 nm, no fluorescence observed from $TiO_2$

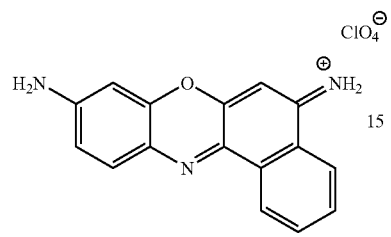

Cresyl Violet

| | |
|---|---|
| CAS Number: | 41830-80-2 |
| Molecular Weight: | 361.74 g/mol |
| Molar Absorption Coefficient: | $6.74 \times 10^4$ L mol$^{-1}$ cm$^{-1}$ @ 601 nm |

Emission in ethanol at 625 nm, no fluorescence observed from $TiO_2$

LDS 698

| | |
|---|---|
| CAS: | 87004-02-2 |
| Molecular Weight: | 378.85 g/mol |
| Molar Absorption Coefficient: | $3.80 \times 10^4$ L mol$^{-1}$ cm$^{-1}$ @ 480 nm |

Emission in ethanol at 660 nm, no fluorescence observed from $TiO_2$

HITCI

| | |
|---|---|
| CAS Number: | 19764-96-6 |
| Molecular Weight: | 536.50 g/mol |
| Molar Absorption Coefficient: | $21.5 \times 10^4$ L mol$^{-1}$ cm$^{-1}$ @ 741 nm |

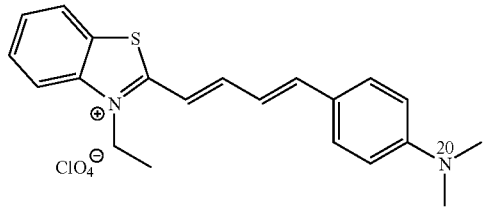

LDS 751

| | |
|---|---|
| CAS: | 76433-29-9 |
| Molecular Weight: | 434.94 g/mol |
| Molar Absorption Coefficient: | $6.15 \times 10^4$ L mol$^{-1}$ cm$^{-1}$ @ 570 nm |

Emission in ethanol at 730 nm, no fluorescence observed from TiO$_2$

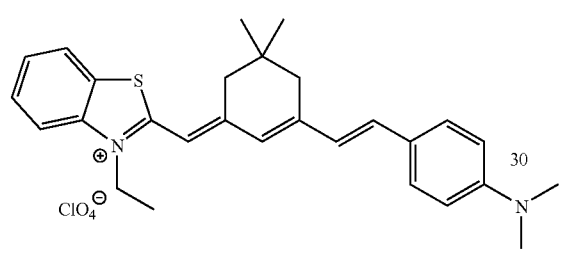

LDS 820

| | |
|---|---|
| CAS: | 76433-25-5 |
| Molecular Weight: | 527.96 g/mol |
| Molar Extinction Coefficient: | $5.05 \times 10^4$ L mol$^{-1}$ cm$^{-1}$ @ 585 nm |

Emission in ethanol at 790 nm, no fluorescence observed from TiO$_2$

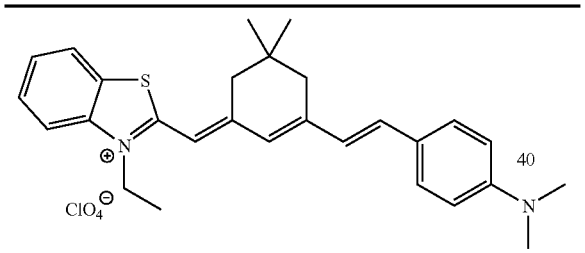

LDS 821

| | |
|---|---|
| CAS: | 120528-73-6 |
| Molecular Weight: | 513.96 g/mol |
| Molar Absorption Coefficient: | $5.05 \times 10^4$ L mol$^{-1}$ cm$^{-1}$ @ 585 nm |

Emission in ethanol at 790 nm, no fluorescence observed from TiO$_2$

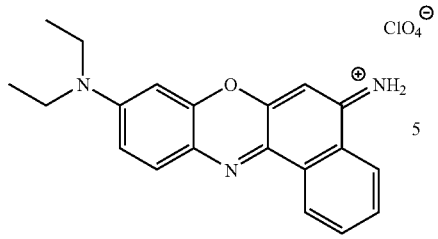

Nile Blue

| | |
|---|---|
| CAS: | 53340-16-2 |
| Molecular Weight: | 417.85 g/mol |
| Molar Absorption Coefficient: | $7.75 \times 10^{\infty 1}$ L mol$^{-1}$ cm$^{-1}$ @ 633 nm |

Emission in ethanol at 670 nm, no fluorescence observed from TiO$_2$

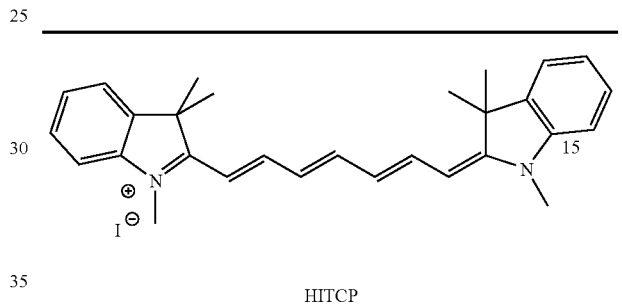

HITCP

| | |
|---|---|
| CAS: | 23178-67-8 |
| Molecular Weight: | 609.17 g/mol |
| Molar Absorption Coefficient: | $23.1 \times 10^4$ L mol$^{-1}$ cm$^{-1}$ @ 780 nm |

Emission in ethanol at 820 nm, also fluoresces on TiO$_2$

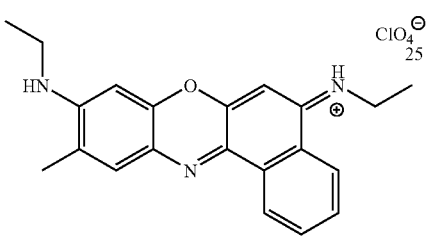

Oxazine 720

| | |
|---|---|
| CAS: | 62669-60-7 |
| Molecular Weight: | 431.87 g/mol |
| Molar Absorption Coefficient: | $9.20 \times 10^4$ L mol$^{-1}$ cm$^{-1}$ @ 627 nm |

Emission in ethanol at 645 nm, no fluorescence observed from TiO$_2$

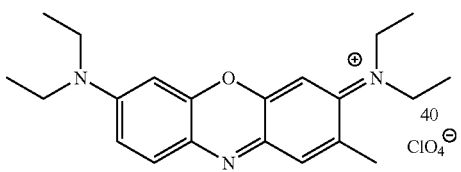

Oxazine 725

| CAS: | 24796-94-9 |
|---|---|
| Molecular Weight: | 423.90 g/mol |
| Molar Absorption Coefficient: | $13.0 \times 10^4$ L mol$^{-1}$ cm$^{-1}$ @ 646 nm |

Emission in ethanol at 660 nm, no fluorescence observed from $TiO_2$

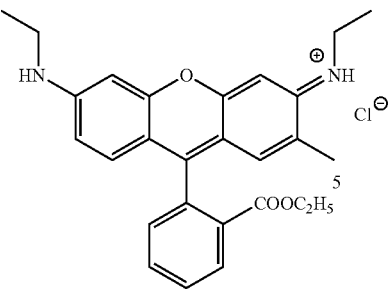

Rhodamine 6G

| CAS: | 989-38-8 |
|---|---|
| Molecular Weight: | 606.71 g/mol |
| Molar Absorption Coefficient: | $10.5 \times 10^4$ L mol$^{-1}$ cm$^{-1}$ @ 533 nm |

Figure 7A:
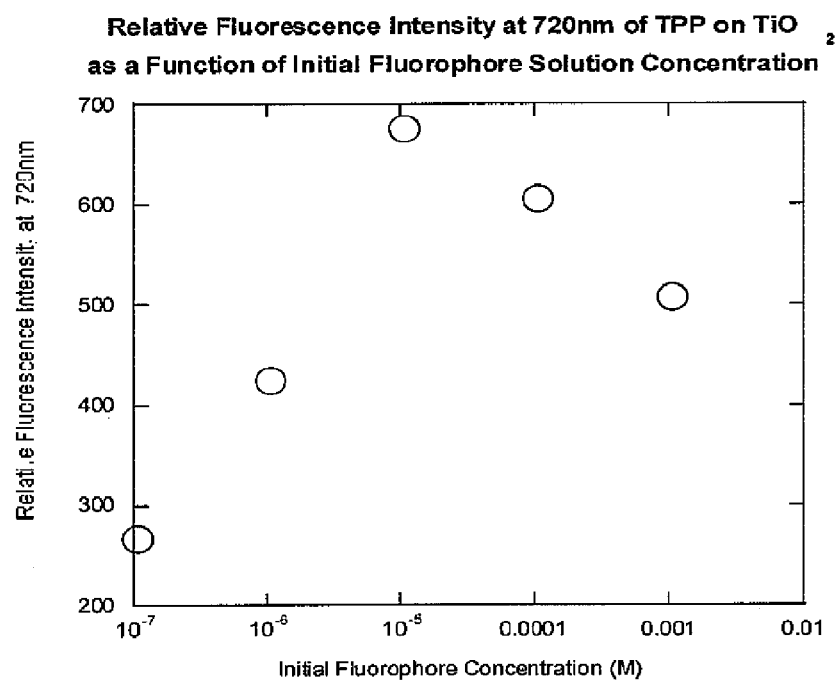
FIG. 7a is a graph of the relative fluorescence intensity at 720 nm of TPP on $TiO_2$ as a function of initial fluorophore solution concentration.
Figure 7B:
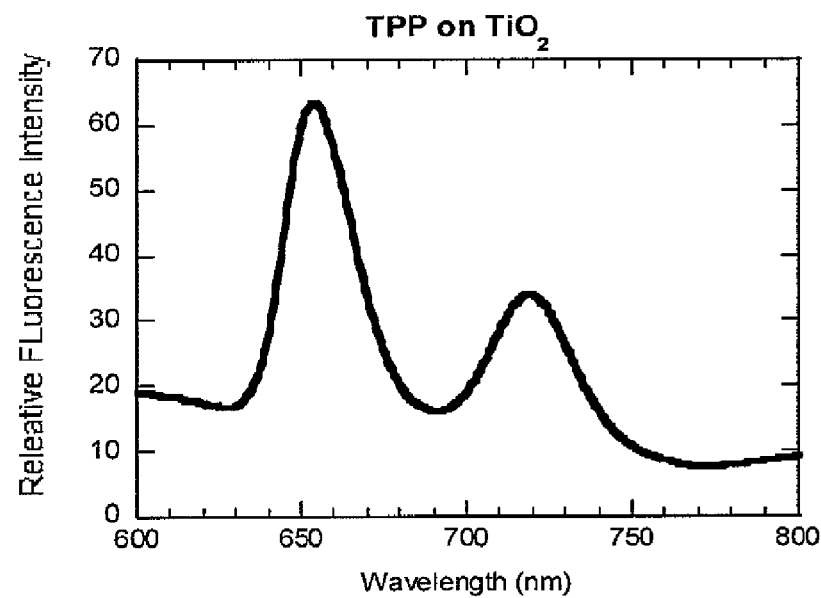
FIG. 7b is a graph of the fluorescence spectra of TPP on $TiO_2$.

Emission in ethanol at 550 nm, weak fluorescence observed from $TiO_2$ Emission on silica and C18 silica acquired at $\lambda_{exc}$ 480 nm is shown in FIG. 7.

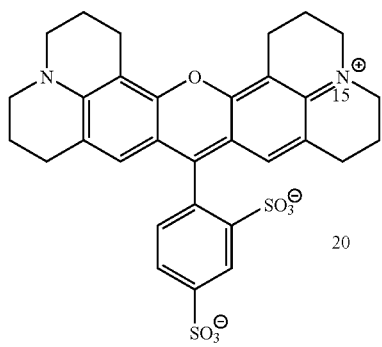

Sulforhodamine 640

| CAS: | 60311-02-6 |
|---|---|
| Molecular Weight: | 606.71 g/mol |
| Molar Absorption Coefficient: | $10.6 \times 10^4$ L mol$^{-1}$ cm$^{-1}$ @ 578 nm |

Emission in ethanol at 590 nm, no fluorescence observed from $TiO_2$

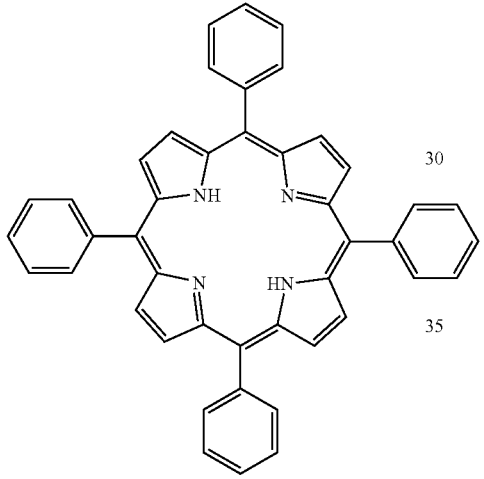

Tetraphenylporphyrin

| CAS: | 917-23-7 |
|---|---|
| Molecular Weight: | 614.74 g/mol |
| Molar Absorption Coefficient: | $18.9 \times 10^3$ L mol$^{-1}$ cm$^{-1}$ @ 415 nm |

The fluorescence from derivatized TiO2 can be as much as four times higher than the underivatized substrate. Fluorescence intensity measurements are not absolute; they require reference to a standard material. (See FIGS. 7a and 7b).

Absorption of Dyes onto Substrate

Several methods have been used to adsorb dyes onto the surface of substrates.

Titanium dioxide ($TiO_2$ 98% rutile, 0.5 gram, 5 μm) was mixed with 4 mL of deionized water. To this mixture was added 1 mL of ethanolic dye solution and shaken vigorously for 3 hours. Mixture was vacuum filtered and vacuum dried for 4 hours at 110° C. and 30 in Hg. The dry powder was stored in an amber vial in a dark cabinet until characterized. Dye concentrations used were 10-100 μM. TPP was added to the powder slurry in ethyl acetate.

Silicon dioxide ($SiO_2$ 0.5 gram, 40 μm) was mixed with 4 mL of ethanol. To this mixture 1 mL of ethanolic dye solution was added and shaken vigorously for 3 hours. Mixture was vacuum filtered and vacuum dried for 4 hours at 65° C. and 30 in Hg. The dry powder was stored in an amber vial in a dark cabinet until characterized. Dye concentrations used were 10-100 μM. TPP was added to the powder slurry in ethyl acetate.

Modification of Substrate

Titanium dioxide particles were derivatized with an eighteen carbon alkane to render them hydrophobic. Alkanes of varying numbers of carbons can also be used to modify titanium dioxide of silicon dioxide particles. $TiO_2$ particles (5 μM) were plasma cleaned in oxygen plasma for three minutes using a Plasma Prep II plasma cleaner. The particles were immediately placed in a vacuum desiccator with a watch glass with ~0.5 mL octadecyltrichlorosilane. The desiccator was sealed and evacuated using a house vacuum overnight. The resulting particles were characterized using ATR-FTIR and stored in a sealed vial until usage.

$C_{18}$ derivatized $SiO_2$ is commercially available as a packing material for reverse phase chromatography. Both $TiO_2$ and $SiO_2$ were treated with dyes as previously described. The derivatized particles are extremely hydrophobic and repel water which can be seen in the photograph of FIG. 2.

Figure 2:
FIG. 2 is a photograph of $SiO_2$—$C_{18}$ with Rhodamine 6G in the presence of water droplets where the powder forms a coating on the droplets, but does not disperse in the water.

FIG. 2 shows $SiO_2$-$C_{18}$ with Rhodamine 6G in the presence of water droplets. The powder forms a coating on the droplets, but will not disperse in the water. It is expected that this property will facilitate binding of the particles to skin and clothing and will be difficult to wash off.

Advanced Taggant

The physisorbed taggant on silica already developed and described above is suitable for a number of applications and can be used to test the imaging system. An advanced taggant uses specific attachment of dye material to the substrate. This material will consist of multiple layers of fluorophores and antioxidants. The spacing between these layers is controlled using linker molecules. Linker molecules comprise metal binding ligands connected by a short alyl chain, for example 4,4'-(ethane-1,2-diylbis(oxy))dipyridine-2,6-dicarboxylic acid. This system can be implemented either on silica or on gold nanoparticles.

The advanced taggant will have enhanced fluorescence, greater stability and features that make counterfeiting more difficult. The use of self assembled multilayers simplifies the design of complex multidimensional systems. Fabricating the taggant on gold nanoparticles has the potential to increase the stability of the taggant and the quantum yield of fluorescence. The use of gold nanoparticles does not significantly increase the cost of the taggant system. We have calculated that one ounce of 300 nm gold nanoparticles, deployed at a density of 1 particle per square millimeter, would yield a strip 2 meters wide and more than 50,000 kilometers long. In short, the gold is not a significant cost component of the taggant.

The advanced taggant uses controlled spacing between fluorophores to modulate energy and electron transfer. The technology is described in U.S. Pat. No. 6,893,716 "Non-covalent assembly of multilayer thin film supramolecular structures" by William Grant McGimpsey and John C. Macdonald, the entire contents of which are hereby incorporated by reference herein. The fluorophores are similar to those that are used for the formation of the physisorbed taggant but are derivatized with a chemistry that will bind metal ions such as chalidamic acid as described in U.S. Pat. No. 6,893,716 and controls electron and energy transfer between components. As a result the same fluorophores may generate a wide range of spectra with different stability. FIG. 3 shows a schematic of a three layer assembly. The fluorophores are represented by the colored circles. The M represents the non covalent linkage between molecules. The chemistry may be assembled on gold, silica, glass or polymer substrates.

Acquisition of Spectra

Fluorescence spectra have been acquired using a modified cuvette shown in FIG. 4. The sample (typically 0.5 gram) is contained in an inner tube within a conventional cuvette. Fluorescence is collected at an angle of 90° to the excitation to minimize scattered light entering the detector.

Particle Labeling

One method to label $TiO_2$ particles is to use hydrophobic and electrostatic interactions. Dyes are dissolved in an organic solvent and mixed with $TiO_2$ particles. The particles are stirred in the solution for 12 hours and then filtered, washed and dried. The fluorescence of the particles is measured in a powder cell. Both excitation and emission spectra are collected to determine the optimum excitation wavelength. The stability of the dye/particle combination is determined by measuring the excitation and emission spectra as a function of irradiation time. The irradiation source is a 250 W Xenon arc lamp filtered to remove wavelengths below 300 nm. The sample holder is jacketed so that the temperature of the sample may be controlled from 4-100° C., Adsorption of dyes onto $TiO_2$ particles has been widely used to construct photochemically active systems for solar energy conversion. In this application, the same techniques are being used to produce dye particles but with the aim of minimizing or controlling the interaction of light with the system. Physisorption of the dye onto the particle surface provides a rapid, economical route to creating relatively complex systems. The technique of fabrication of chemically derivatized surfaces may also be used. This technology allows for more complex combinations of dyes and other materials to be precisely controlled. The physical adsorption of dyes onto the surface is simple and because the sample is a solid, diffusion kinetics need not be considered in designing stable fluorescent entities.

Fluorescence Measurement

The fluorescence properties of the particles are monitored using both steady state and time resolved instrumentation. The steady state characterization uses a Perkin Elmer LS-50B Spectrofluorometer. Following the development of promising dye/particle systems, time resolved fluorescence spectra is obtained using a Photon Technology International TM3/2005 equipped with a dye pumped nitrogen laser. The instrument is capable of determining lifetimes as short as 100 ps. This is an important tool for determining combinations and concentrations of dyes and lifetime modifiers as well as $TiO_2$ crystal type, i.e. rutile and anatase.

Photostability

The average power of the sun that reaches the earth in certain climatic conditions is approximately 300 $W/m^2$. Of this energy about 50% is in the visible region of the electromagnetic spectrum. Therefore, the incident power of solar radiation is about 15 $mW/cm^2$. Laser dyes are designed to be stable at powers significantly greater than this. For example, tests have been done on the stability of a number of laser dyes at peak laser intensities of 20-100 $kW/cm^2$. The measured quantum yields of degradation are around $1\times10^{-6}$ dye molecules bleached per photon absorbed. In other words, it would take a million absorbed photons to destroy a dye molecule.

Using these figures it is possible to estimate to within an order of magnitude the stability of the dyes. The taggant is considered to be made up of a single molecular film of dye. Such films made up of a dye with a molar absorption coefficient of $10^5$ $M^{-1}$ $cm^{-1}$ has an absorption of about 0.01. This means that the film will absorb about 2% of the light incident on it. If the wavelength of the average visible photon is 500 nm, then the number of photons incident at 15 $mW/cm^2$ will be $3.78\times10^{16}$. Only 2% of these will be absorbed by the film so there will be $7.56\times10^{14}$ photons absorbed. If the quantum yield of degradation is $10^{-6}$ then it will take $10^5$ seconds or about 28 hours for 10% of the dye to degrade.

There are a number of factors which will affect this estimate. The quantum yield of degradation is given for solution phase chemistry; solid films are likely to be significantly more stable. If the average daytime temperature is about 120° F. (48° C.), dyes are likely to be less stable at such elevated temperatures.

Photostability studies can be carried out by irradiating samples with broadband light to simulate solar radiation at a range of powers centered around 15 $mW/cm^2$ and at room temperature (20° C.) and at elevated temperatures. The ideal taggant will degrade at a constant rate irrespective of the light that falls on it and the temperature to which it is subjected. The taggant will be most sensitive to the amount of light it is irradiated with and less so to the temperature. This is because in solid phase chemistry there is little or no diffusion which is the factor that makes solution phase chemistry most sensitive to temperature. By carefully controlling the spacing of the dyes on the particle surface one can determine the processes that lead to dye degradation and dye stability.

Control of Stability

Following absorption of a photon a molecule is promoted to an excited state. The processes that occur following excitation determine the stability of the dye. Fluorescence or emission of heat (non radiative decay) return the dye to the ground state and leaves the dye unaltered. For a dye that is in the solid state, the processes that can lead to destruction of the dye are reaction of the excited state with another excited state or reaction with a ground state molecule. It is also possible to control the stability of a dye by colocalizing the dye with antioxidants or redox active materials. Finally, there are two commonly available crystalline forms of $TiO_2$. These are rutile and anatase $TiO_2$. The rutile form is relatively photochemically inert and leads to a more stable dye/particle complex. There are a number of strategies to control the length of time that a dye on a $TiO_2$ particle remains fluorescent.

A range of dye/particle mixtures are available that have a predictable degradation rate. Because the temperature and intensity of the sunlight vary considerably between the winter and summer months, the taggant is produced in two variants suitable for each season. Since the primary degradation mechanisms involve photochemical and thermal mechanisms it is also possible to utilize these taggants in the "wrong" season as long life and short life taggants respectively.

The approaches to control the lifetime of the taggant are summarized in Table 1:

TABLE 1

| Increase Stability | Decrease Stability |
| --- | --- |
| Rutile $TiO_2$ | Anatase $TiO_2$ |
| Low dye concentration | High dye concentration |
| Different dyes on different particles | Co-localize dyes |
| Co-localize antioxidants | Co-localize redox active agents |

Radiometric Monitoring

Monitoring of fluorescence intensity alone is problematic since fluorescence is not an absolute technique and cannot be quantitated unless compared to a standard fluorescing material. There are two widely accepted approaches to this problem. The first is to utilize time resolved spectroscopy and measure the excited state lifetime. The second is to use a combination of dyes and ratio the relative intensities of the two dyes.

Monitoring the excited lifetime increases the complexity of the monitoring system but gives extremely reliable data. Commercially available hyperspectral imaging systems may be used to image the fluorescent taggant and ascertain its authenticity by comparing the relative intensity of different regions of the spectrum through ratiometric means.

Toxicity

A critical factor in spraying taggants is that there is no environmental impact of the material. The choice of designing unique, fluorescent, coded systems with $TiO_2$ is deliberate. $TiO_2$ is widely used today in the environment at high concentrations in the presence of a wide range of dyes. $TiO_2$ is used in cosmetics, paints, as a filler in drug formulations and as a whitening agent for paper. The dyes used are present at low concentration and many of them are actually related to food dyes as well as other coloring applications. The application of the material is at low concentration, thereby limiting the environmental impact.

Transfer of Taggant to Individuals

The ability to chemically modify the surface of the particles allows one to make the surface hydrophobic or hydrophilic, electrostatically positive or negative. These properties may be exploited to provide intelligence data of routes to and from the suspected IED threat region by designing the dye/particle to adhere to an individual who tampers with the taggant. Alternatively, where individuals are involved in an ambush scenario, their vehicles may be deliberately tagged to prevent them from disappearing into civilian crowds.

IV. Method of Making

Three dyes are formulated with $TiO_2$ particles in the anatase form and the rutile form. This is achieved by dissolving the dyes in ethanol solution and stirring them with the $TiO_2$ powder for twelve hours. The samples are then filtered, washed and dried. The excitation and emission spectra of these six samples are measured and then the samples irradiated using a xenon arc lamp at an average power of 15 $mW/cm^2$. The decomposition of the dyes are then determined from the change in the excitation and emission spectra of the samples. In this way, the simplest formulations of dye and $TiO_2$ are assessed for stability. The dye-rutile samples are significantly more stable than the dye-anatase samples. The temperature dependence is also determined at an elevated temperature of 50° C.

The ratiometric monitoring of the fluorescence excitation and emission spectra of different dye-$TiO_2$ particle mixtures is demonstrated. With individual dyes located on different particles there is no interactions of different dyes. Different dyes decay at different rates on the $TiO_2$ particles and therefore monitoring of the relative intensities of the two dyes allows one to measure the length of time a powder mixture has been deployed.

First, two dyes are co-localized on the same particle (coding) followed by the co-localization of antioxidants and redox active agents to finely control the lifetime of the taggant.

The co-localization of dyes onto the same particle effectively creates a new fluorescent system that can only be duplicated by following the preparation methods exactly. This is because dye—dye interactions cause energy and electron transfer pathways to be created in these systems. The result is that the system has a fluorescence excitation and emission spectrum which is dependent on how the dyes are localized on the surface of the particles. These interactions are dependent on the concentrations of the dyes when applied to the $TiO_2$ powder and geometry of the particle surface. Unless the source of the $TiO_2$ can be duplicated it is very difficult to mimic or forge the photophysical behavior of the dye particle system.

Precise control of the degradation time of the fluorescent taggant is controlled by incorporation of antioxidant and redox active materials. The primary mechanism by which dyes photobleach is electron transfer. Co-localization of antioxidants such as butylated hydroxytoluene (BHT) with the dye $TiO_2$ can quench electron transfer reactions thereby improving the lifetime of the dye. BHT is a useful antioxidant for this purpose since it does not decompose on exposure to air. It is commonly applied to the packaging of foodstuffs to prevent oxidation. It has been proposed that BHT is effective in this role since it only reacts with strong oxidants and is therefore ideal in a photoreactive system.

Design of the Imaging System

Detection of fluorescence light will be achieved using a large optic (100 mm aperture). It is estimated that for a single fully loaded 40 μm taggant particle, at a distance of 3 meters, with photons emitted from every particle the lens will collect 80,000 photons. This is readily detectable using phase sensitive detection which allows for time resolved data to be collected.

The detector will be a photomultiplier tube coupled to a high throughput spectrograph (in house). The output of the PMT is connected to an RF lock-in amplifier and thence to a computer. Analysis of the data will be carried out for phase shift and depth of modulation which are both related to the lifetime of the fluorophore.

Concept of Employment

Figure 8:
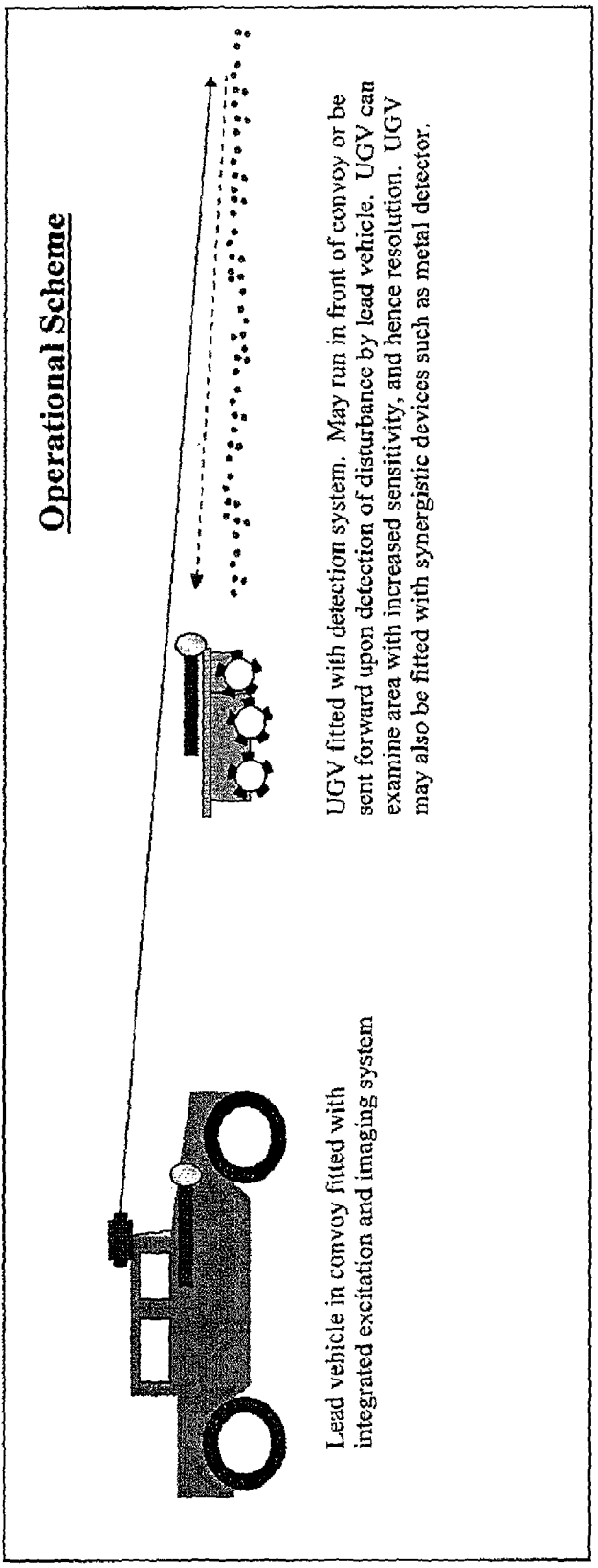
FIG. 8 is a schematic view of a field system suitable for use with the present invention.

The schematic of FIG. 8 summarizes how the system might be used in the field. The system may operate either by detecting a disturbance in the deployed region or the presence of a taggant in the non deployed region. Coincident detection of a disturbance and the presence of a taggant increases the probability that a disturbance has occurred. It is also possible to deploy taggant underground. If for example a road surface is repaired and the taggant is deployed beneath the surface then the presence of taggant would indicate a disturbance.

The material will be deployed in a liquid to enable targeted, precise distribution and to prevent loss of material due to wind. The coverage is extremely low with a typical density of 1 particle per square centimeter. A low coverage density decreases the probability that the material could be swept up in quantities large enough to be analyzed by an enemy. The detector consists of an excitation laser and a detector. The laser is scanned across the ground up to 300 meters in front of the convoy. Both back scattered UV light and fluorescence is detected using avalanche photodiodes. The excitation source is modulated which allows temporal data to be detected. The UV scattered light is monitored so that changes in the temporal profile of the excitation source and the emission may be compared. This information is used to calculate the apparent fluorescence lifetime of the irradiated area.

What is claimed is:

1. A method of identifying changes comprising:
dispersing a taggant;
detecting a taggant signal;
recording a first signal;
detecting a second signal;
recording said second signal;
comparing said first signal to said second signal; and
identifying differences between said first signal and said second signal;
wherein said taggant signal fades or degrades over time.

2. The method of claim 1, wherein said taggant is a composition comprising one or more fluorophores and a substrate.

3. The method of claim 1, wherein said taggant is not detectable by the unaided eye.

4. The method of claim 1, wherein said taggant further comprises an odorant.

5. The method of claim 1, wherein said taggant comprises one or more fluorophores and a substrate.

6. The method of claim 5, wherein said one or more fluorophores is a laser dye.

7. The method of claim 6, wherein said one or more dye is selected from the group consisting of tetraphenylporphyrin, indodicarbocyanine, indotricarbocyanine, HITCI, HITCP, and Rhodamine 6G.

8. The method of claim 5, wherein said substrate is metal nanoparticles, a semiconductor or an insulator.

9. The method of claim 8, wherein said semiconductor is titanium dioxide.

10. The method of claim 9, wherein said insulator is selected from the group consisting of gold, silica, PVA and hydroxyceilulose.

11. The method of claim 5, wherein said substrate further comprises an alkane.

12. The method of claim 1, wherein said taggant further comprises an antioxidant or redox active material.

13. The method of claim 12, wherein said antioxidant is butylated hydroxytoluene.

14. The method of claim 1, Wherein said dispersing is by spreading, spraying, or dusting.

15. A composition comprising one or more fluorophores and a substrate, wherein said substrate comprises alkane derivatized titanium dioxide particles or alkane derivatized silicon dioxide particles.

16. The composition of claim 15, wherein said one or more fluorophores is a laser dye.

17. The composition of claim 16, wherein said one or more dye is selected from the group consisting of tetraphenylporphyrin, indodicarbocyanine, indotricarbocyanine, HITCI, HITCP, and Rhodamine 6G.

18. The composition of claim 15, further comprising an antioxidant or a redox active material.

19. The composition of claim 18, wherein said antioxidant is butylated hydroxytoluene.

20. A method of identifying changes comprising:
dispersing a taggant;
detecting a taggant signal;
recording a first signal;
detecting a second signal;
recording said second signal;
comparing said first signal to said second signal; and
identifying differences between said first signal and said second signal;
wherein said taggant further comprises an odorant.

* * * * *

UNITED STATES PATENT AND TRADEMARK OFFICE
CERTIFICATE OF CORRECTION

PATENT NO. : 8,362,447 B2  
APPLICATION NO. : 12/668938  
DATED : January 29, 2013  
INVENTOR(S) : Christopher R. Lambert Page 1 of 1

It is certified that error appears in the above-identified patent and that said Letters Patent is hereby corrected as shown below:

In Column 16, line 13 (claim 10), "The method of claim 9" should read -- The method of claim 8 --

In Column 16, line 15 (claim 10), "hydroxyceilulose" should read -- hydroxycellulose --

Signed and Sealed this  
Twenty-sixth Day of March, 2013

Teresa Stanek Rea  
*Acting Director of the United States Patent and Trademark Office*